(12) United States Patent
Abe et al.

(10) Patent No.: US 8,859,221 B2
(45) Date of Patent: Oct. 14, 2014

(54) METHOD FOR MEASURING HIGH DENSITY LIPOPROTEIN CHOLESTEROL

(75) Inventors: Yoshihiko Abe, Asaka (JP); Nobuhito Masuda, Asaka (JP); Hiroko Inomata, Asaka (JP)

(73) Assignee: FUJIFILM Corporation, Tokyo (JP)

( * ) Notice: Subject to any disclaimer, the term of this patent is extended or adjusted under 35 U.S.C. 154(b) by 21 days.

(21) Appl. No.: 11/798,141

(22) Filed: May 10, 2007

(65) Prior Publication Data

US 2007/0275429 A1      Nov. 29, 2007

(30) Foreign Application Priority Data

May 10, 2006   (JP) ................................ 2006-131123

(51) Int. Cl.
*C12Q 1/60*       (2006.01)
*G01N 33/92*    (2006.01)

(52) U.S. Cl.
CPC . *C12Q 1/60* (2013.01); *G01N 33/92* (2013.01)
USPC ................. 435/11; 435/4; 435/190; 435/192; 435/197

(58) Field of Classification Search
None
See application file for complete search history.

(56) References Cited

U.S. PATENT DOCUMENTS

| | | | |
|---|---|---|---|
| 4,511,655 A * | 4/1985 | Minai et al. | 435/149 |
| 5,807,696 A * | 9/1998 | Miyauchi et al. | 435/11 |
| 6,939,682 B2 | 9/2005 | Tamura et al. | |
| 7,575,884 B2 | 8/2009 | Tamura et al. | |
| 2004/0023400 A1 | 2/2004 | Tamura et al. | |
| 2004/0224137 A1 * | 11/2004 | Rogalska et al. | 428/209 |
| 2005/0250165 A1 | 11/2005 | Tamura et al. | |
| 2008/0135419 A1 * | 6/2008 | Roblin et al. | 205/777.5 |

FOREIGN PATENT DOCUMENTS

| | | | |
|---|---|---|---|
| CN | 1473200 A | | 2/2004 |
| JP | 52014490 A | * | 2/1977 |
| JP | 53-9391 A | | 1/1978 |
| JP | 2005-137360 A | | 6/2005 |
| WO | WO 00/73797 A2 | | 12/2000 |

OTHER PUBLICATIONS

Chinese Office Action, dated Jul. 6, 2011, for Chinese Application No. 200710129287.8
Lolekha et al., "Optimization Studies of Components in Enzymatic Cholesterol Reagents Containing Cholesterol Oxidase From Nocardia erythropolis, *Streptomyces* sp, or *Pseudomonas fluorescens*", Journal of Clinical Laboratory Analysis, vol. 10, pp. 167-176, 1996.
Office Action for Japanese Application No. 2007-122183, dated Jul. 24, 2012, including partial English translation.

* cited by examiner

*Primary Examiner* — Lisa J Hobbs
(74) *Attorney, Agent, or Firm* — Birch, Stewart, Kolasch & Birch, LLP

(57) ABSTRACT

An object to be attained by the present invention is to provide a method for conveniently, rapidly, and specifically measuring HDL-C in a specimen by use of inexpensive materials, and to provide a reagent kit for HDL-C detection and a dry analytical element for HDL-C detection. The present invention provides a method for measuring high density lipoprotein cholesterol (HDL-C) in a body fluid test sample, wherein cholesterol esterase derived from *Schizophyllum commune* or *Pseudomonas* sp. and cholesterol oxidase derived from *Pseudomonas* sp. are used to generate hydrogen peroxide from HDL-C, and thereby HDL-C is selectively measured.

7 Claims, 6 Drawing Sheets

METHOD FOR MEASURING HIGH DENSITY LIPOPROTEIN CHOLESTEROL

TECHNICAL FIELD

The present invention relates to a method for measuring high density lipoprotein cholesterol (HDL-C) in a specimen. The serum level of high density lipoprotein cholesterol is known to serve as an index useful for predicting the onset of arteriosclerotic diseases.

BACKGROUND ART

Lipids present in blood are incorporated in the structure of lipoprotein, except for free fatty acid bound with albumin, and are present as chylomicron (CHM), very low density lipoprotein (VLDL), low density lipoprotein (LDL), high density lipoprotein (HDL), and the like. Cholesterol therein is particularly distributed in VLDL, LDL, and HDL. HDL is allegedly a preventive factor for heart diseases attributed to arteriosclerosis. Thus, the measurement of high density lipoprotein cholesterol (HDL-C) instead of HDL clinically has a more important meaning. Ultracentrifugation, electrophoresis, and precipitation methods are widely known as current methods for measuring HDL-cholesterol.

The ultracentrifugation method is not suitable for daily examination for such reasons that: it requires a long time for separation procedures; and inexpensive measurement cannot be expected because an apparatus itself is expensive. The electrophoresis method still has a problem in light of quantification for such reasons that: its separation ability differs depending on a difference in electrophoresis support medium; and the method differs depending on use conditions and detection reagents used. Thus, the precipitation method is widely used as current daily examination.

The precipitation method is a method comprising using, for example, a combination of a polyanion and a divalent metal ion, as a precipitating reagent to precipitate CHM, LDL, and VLDL and measuring cholesterol in HDL, that is, HDL-cholesterol, remaining in the supernatant by use of a chemical reagent or enzyme. A combination of a sulfated polysaccharide and an alkaline earth metal ion or a divalent metal ion other than alkaline earth, an inorganic polyanion salt, polyethylene glycol, and so on, which have been well known since the early 1960s by T. Nakai, "HDL-Metabolism, Assay Methods and Clinical Application" (Chugaiigaku Co., Ltd., 1986) and other various documents and textbooks, are widely used as the precipitating reagent. Specific examples of the precipitating reagent include a heparin-calcium reagent, a dextran sulfate-magnesium reagent, and a phosphotungstic acid-magnesium reagent.

The precipitation method is a method in which serum is mixed with the precipitating reagent and left for a certain period of time, and after centrifugation at approximately 3000 revolutions per minute, an aliquot of the supernatant portion is separated and subjected to chemical reaction or enzyme reaction to quantify HDL-cholesterol.

The precipitation method presents problems derived from the precipitating reagent and problems derived from centrifugation procedures. Therefore, JP Patent Publication (Kokai) Nos. 55-78254A (1980), 55-93065A (1980), 61-263467A (1986), and 62-19768A (1987), JP Patent Publication (Kokoku) No. 1-39553B (1989), etc. have described various methods for improving precipitating agents for enhancing precipitation efficiency.

The major disadvantage of the conventional precipitation method is that the use of a reagent rich in triglyceride sometimes results in the partial floating of precipitates after centrifugation. Therefore, the precipitation method presents such a big problem that the adjustment of centrifugation conditions is required. In a method using phosphotungstate-magnesium ions, precipitation sometimes varies depending on the pH of the solution. Therefore, the method presents such a problem that the strict adjustment of pH is required.

When a centrifuged supernatant, particularly a small amount of the supernatant, is separated, the boundary region between precipitates and the supernatant is difficult to determine by visual observation. Therefore, quantitative analysis precision is sometimes lowered due to reproducibility and precision problems and variations among individuals. It has been demanded to improve these disadvantages attributed to centrifugation procedures.

A direct method that does not require these complicated procedures and is available for an automatic analyzer has spread rapidly in recent years. For example, JP Patent Publication (Kokai) No. 8-131197A (1996) has disclosed a method comprising sufficiently reacting sulfated cyclodextrin used as an aggregating agent with lipoprotein other than HDL, then allowing an enzyme modified with polyoxyethylene glycol to act thereon, and measuring cholesterol in HDL. WO98/26090 has disclosed a method comprising a first step of eliminating lipoprotein other than HDL by use of catalase and a second step of measuring HDL-C by use of an activator that specifically acts on HDL. Furthermore, JP Patent Publication (Kokai) No. 9-96637A (1997) has described a method comprising initially allowing an antibody against lipoprotein other than HDL to act thereon, subsequently dissolving HDL, and measuring cholesterol in HDL.

However, these methods required using expensive reagents such as enzymes modified with PEG and antibodies, for suppressing reaction from lipoprotein other than HDL.

The precipitation method was also in the mainstream in the field of dry chemistry. However, a novel test piece for a dry process using the direct method has been developed in recent years and described in JP Patent No. 3686326. JP Patent Publication (Kokai) No. 2005-137360A (2005) has disclosed that the use of lipase derived from *Candida rugosa* improves selectivity. However, any of the test pieces cannot completely remove cholesterol in lipoprotein other than HDL.

DISCLOSURE OF THE INVENTION

An object to be attained by the present invention is to provide a method for conveniently, rapidly, and specifically measuring HDL-C in a specimen by use of inexpensive materials, and to provide a reagent kit for HDL-C detection and a dry analytical element for HDL-C detection.

The present inventors have conducted diligent studies for attaining the object and have consequently found that the use of cholesterol esterase derived from *Schizophyllum commune* or *Pseudomonas* sp. and cholesterol oxidase derived from *Pseudomonas* sp. as enzymes for HDL-C detection allows for the efficient and selective measurement of cholesterol in HDL. The present invention has been completed on the basis of these findings.

The present invention provides a method for measuring high density lipoprotein cholesterol (HDL-C) in a body fluid test sample, wherein cholesterol esterase derived from *Schizophyllum commune* or *Pseudomonas* sp. and cholesterol oxidase derived from *Pseudomonas* sp. are used to generate hydrogen peroxide from HDL-C, and thereby HDL-C is selectively measured.

Preferably, a surfactant that preferentially dissolves high density lipoprotein (HDL) is used.

Preferably, the surfactant that preferentially dissolves HDL is polyoxyethylene alkylene phenyl ether or polyoxyethylene alkylene tribenzyl phenyl ether.

Preferably, polyoxyethylene alkylene phenyl ether is polyoxyethylene styryl phenyl ether, and polyoxyethylene alkylene tribenzyl phenyl ether is polyoxyethylene tribenzyl phenyl ether.

Preferably, polyoxyethylene styryl phenyl ether is polyoxyethylene mono-, di-, or tri-styryl phenyl ether.

Preferably, a surfactant that inhibits the lipoprotein other than high density lipoprotein (HDL) from dissolving and/or an aggregating agent that aggregates lipoprotein other than HDL are used.

Preferably, the surfactant that inhibits the lipoprotein other than high density lipoprotein (HDL) from dissolving is polyoxyethylene alkyl ether sulfate, alkylbenzene sulfonate, or a polyoxyethylene-polyoxypropylene condensate.

Preferably, the aggregating agent that aggregates lipoprotein other than HDL is phosphotungstic acid or a salt thereof combined with a divalent metal ion, dextran sulfate combined with a divalent metal ion, heparin combined with a divalent metal ion, or polyoxyethylene.

Preferably, HDL-C is measured through color reaction in which peroxidase and chromogens are allowed to act on the hydrogen peroxide generated from HDL-C by the cholesterol esterase and the cholesterol oxidase.

Preferably, the chromogens used are 4-aminoantipyrine or a derivative thereof and a Trinder reagent that couples with the 4-aminoantipyrine or the derivative thereof.

Preferably, HDL-C is measured by use of a dry analytical element comprising at least an adhesive layer and a porous developing layer on a water-impermeable support.

An alternative aspect of the present invention provides a reagent kit for HDL-C detection comprising at least cholesterol esterase derived from *Schizophyllum commune* or *Pseudomonas* sp. and cholesterol oxidase derived from *Pseudomonas* sp.

A further alternative aspect of the present invention provides a dry analytical element for HDL-C detection comprising at least an adhesive layer and a porous developing layer on a water-impermeable support, wherein cholesterol esterase derived from *Schizophyllum commune* or *Pseudomonas* sp. and cholesterol oxidase derived from *Pseudomonas* sp. are contained in the layer(s) on the water-impermeable support.

BEST MODE FOR CARRYING OUT THE INVENTION

Figure 1:
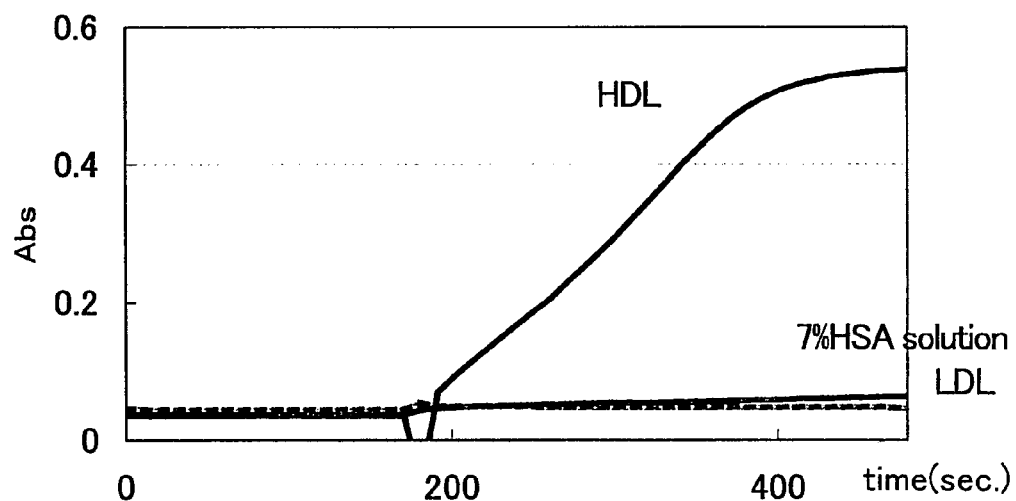
FIG. 1 shows a result of a measurement example (Examples 1) of a solution system using enzymes of the present invention.

Hereinafter, the embodiments of the present invention will be described in detail.

A method for measuring high density lipoprotein cholesterol (HDL-C) according to the present invention is characterized in that cholesterol esterase derived from *Schizophyllum commune* or *Pseudomonas* sp. and cholesterol oxidase derived from *Pseudomonas* sp. are used to generate hydrogen peroxide from HDL-C, and thereby HDL-C is selectively measured.

In the present invention, HDL-C in a body fluid test sample can be measured. Blood or urine or the like can be used as the body fluid. Blood or urine may be used directly as a body fluid test sample or may be used as a body fluid test sample after appropriate pretreatment.

Next, reagents used in the method of the present invention will be described.

Enzymes used in the present invention are cholesterol esterase and cholesterol oxidase. Cholesterol esterase derived from *Schizophyllum commune* or *Pseudomonas* sp. is used as the cholesterol esterase of the present invention. Cholesterol esterase derived form *Schizophyllum commune* is particularly preferable. Cholesterol oxidase derived from *Pseudomonas* sp. is used as the cholesterol oxidase of the present invention. Any of the enzymes used in the present invention may be an enzyme derived from each of the microorganisms or may be a recombinant product produced by a well known method.

Examples of the cholesterol esterase derived from *Schizophyllum commune* include COE-302 manufactured by TOYOBO Co., Ltd. Examples of the cholesterol esterase derived from *Pseudomonas* sp. include COE-311, LPL-312 and LPL-314 manufactured by TOYOBO Co., Ltd, and CEN manufactured by Asahi Kasei Corp. Examples of the cholesterol oxidase derived from *Pseudomonas* sp. include CHO-PEL and CHO-PEWL manufactured by Kikkoman Corp.

In the present invention, it is preferred that a surfactant that preferentially dissolves HDL should be used. Polyoxyethylene alkylene phenyl ether (formula 1) and polyoxyethylene alkylene tribenzyl phenyl ether (formula 2) can be used as the surfactant that preferentially dissolves HDL.

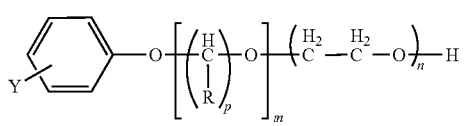

(Formula 1)

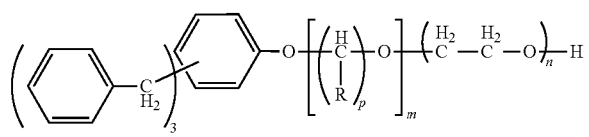

(Formula 2)

Y in Formula 1 may include hydrogen atom, halogen atom, alkyl, alkene, phenyl, heterocyclic group, hydroxyl, alkyloxy, phenyloxy, amino, alkylamino, cyano, carbonyl, carbonyloxy, alkyloxycarbonyl, and the like. R may include hydrogen atom and C1-C8 alkyl and may be the same or different in a same molecule. P represents 2 to 6, m represents 0 to 2, and n represents 5 to 100.

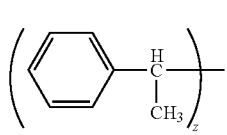

(Formula 3)

The addition mole number (z) of styryl group of Formula 3 is preferably 1 to 5. Polyoxyethylene mono-, di-, or tri-styryl phenyl ether which corresponds to Z=1 to 3 is further preferred.

It is particularly preferred that Y in Formula 1 is a styryl group (formula 3) and the addition mole number (m) of polyoxyalkylene is 0. Namely, polyoxyethylene styryl phenyl ether is preferred. The average (n) of the addition mole number of polyoxyethylene ii preferably 5 to 100, and n is preferably 5 to 50, and is particularly preferably 10 to 50.

n may be a single number, or may be different numbers. Namely, the surfactant may be a mixture of several compounds. For example, commercially available products of polyoxyethylene styryl phenyl ether include Noigen EA-157 manufactured by Dai-ich Kogyo Seiyaku Co., Ltd wherein the average addition mole number of polyoxyethylene is 17 and n represents about 5 to about 30. Namely, this product is a mixture of several compounds.

Particularly preferred example of Formula 2 is polyoxyethylene tribenzyl phenyl ether wherein the addition mole number (m) of polyoxyalkylene is 0. The average addition mole number (n) of polyoxyethylene of formula 2 is preferably 5 to 100, and further preferably 5 to 50, and particularly preferably 10 to 50. n may be a single number, or may be different numbers. Namely, the surfactant may be a mixture of several compounds. For example, commercially available products of polyoxyethylene tribenzyl phenyl ether include Emulgen B66 manufactured by Kao Corp wherein the average addition mole number of polyoxyethylene is 16 and n represents about 5 to about 30. Namely, this product is a mixture of several compounds.

Examples of the commercially available products of the aforementioned surfactant include Paionin D-6512 (manufactured by Takemoto Oil & Fat Co., Ltd) as polyoxyethylene monostyryl phenyl ether; Noigen EA-157 and Emulgen A90 (manufactured by Kao Corp.) as polyoxyethylene distyryl phenyl ether; Sorpol T20 (manufactured by TOHO Chemical Industry Co., Ltd) and Newcol 2609 (manufactured by Nippon Nyukazai Co., Ltd) as polyoxyethylene tristyryl phenyl ether; and Emulgen B66 and Pegnol 005 (manufactured by TOHO Chemical Industry Co., Ltd) as polyoxyethylene tribenzyl phenyl ether.

These surfactants can be used alone or may be used as a mixture.

In the present invention, a surfactant that inhibits the lipoprotein other than high density lipoprotein (HDL) from dissolving can be used. Examples of the surfactant that inhibits the lipoprotein other than high density lipoprotein (HDL) from dissolving include surfactants selected from polyoxyethylene alkyl ether sulfate, alkylbenzene sulfonate, and a polyoxyethylene-polyoxypropylene condensate. Examples of the polyoxyethylene alkyl ether sulfate include EMAL 20C (manufactured by Kao Corp.). Examples of the polyoxyethylene-polyoxypropylene condensate include Pluronic series (manufactured by ADEKA Corp.).

In the present invention, an aggregating agent that aggregates lipoprotein other than HDL can be used. A combination of a sulfated polysaccharide and an alkaline earth metal ion or a divalent metal ion other than alkaline earth, an inorganic polyanion salt, polyethylene glycol, and so on, which have been well known since the early 1960s by T. Nakai, "HDL-Metabolism, Assay Methods and Clinical Application" (Chugaiigaku Co., Ltd., 1986) and other various documents and textbooks, can be used as the aggregating agent that aggregates lipoprotein other than HDL.

Of these precipitating reagents, precipitating reagents such as a dextran sulfate-calcium (2+) ion complex described in "Journal of Laboratory and Clinical Medicine" Vol. 82, p. 473-(1973), a dextran sulfate-magnesium (2+) ion complex described in "J. Lipid Res." Vol. 11, p. 583-595 (1970), "Clin. Chem." Vol. 24, p. 931-933 (1978), etc., heparin alone or a combination of heparin sodium and a manganese ion described in "J. Lipid Res." Vol. 11, p. 583-595 (1970) and "Manual of Lipid Operations. Lipid Research Clinics Program. Volume I" Pub. No. (NIH) 75-628 (1978), and a combination of heparin, a calcium ion, and a nickel (2+) ion described in JP Patent Publication (Kokai) No. 55-51359A (1980) are preferable as the combination of a sulfated polysaccharide and a metal ion. A combination of phosphotungstic acid (phosphotungstate) and a magnesium (2+) ion described in "J. Lipid Res." Vol. 11, p. 583-595 (1970), "Clin. Chem." Vol. 23, p. 882-884 (1977), "Clin. Chem." Vol. 25, p. 939-942 (1979), U.S. Pat. No. 4,226,713, JP Patent Publication (Kokoku) No. 63-27659B (1988) (U.S. Pat. No. 4,215, 993), JP Patent Publication (Kokai) No. 01-39553A (1989) (U.S. Pat. No. 4,251,519), etc. is preferable as the inorganic polyanion salt precipitating reagent. More preferable examples thereof include dextran sulfate combined with a magnesium ion.

In the present invention, a well known enzyme reagent, chromogens, and pH buffer can be used as reagents for cholesterol detection, in addition to these reagents.

Specifically, examples of the enzyme include peroxidase. Examples of the chromogens include 4-aminoantipyrine (4-AA) and a phenolic or anilinic Trinder reagent that develops color though hydrogen-donating coupling therewith. Preferably, the Trinder reagent is an anilinic reagent. Examples thereof include ADPS, ALPS, TOPS, ADOS, DAOS, HDAOS, MAOS, and TOOS manufactured by DOJINDO Laboratories.

Examples of the pH buffer include carbonate, sulfate, phosphate, and Good's pH buffers described in "Biochemistry" Vol. 5 (No. 2), p. 467-477 (1966). These pH buffers can be selected with reference to the descriptions of documents such as "Basic Experimental Methods of Proteins and Enzymes" (T. Horio et al., Nankodo Co., Ltd., 1981) and "Biochemistry" Vol. 5.

The pH of the buffer is determined depending on the optimum pH of the enzyme used and adjusted to preferably 5.0 to 8.0, more preferably 6.0 to 7.0.

Next, the measurement method of the present invention using a solution as a measurement system will be described. A solution with composition comprising the following (1) to (6) as the composition of a reagent solution is preferable:
(1) cholesterol esterase derived from *Schizophyllum commune* or *Pseudomonas* sp.
(2) cholesterol oxidase derived from *Pseudomonas* sp.
(3) surfactant that preferentially dissolves HDL
(4) peroxidase
(5) chromogens (4-AA and Trinder reagent)
(6) pH buffer A 1 to 1000 µL aliquot, preferably a 100 to 500 µL aliquot of the reagent solution comprising these reagents adjusted to the optimum concentrations is incubated in advance at a constant temperature ranging from approximately 20° C. to approximately 45° C., preferably approximately 30° C. to approximately 40° C., for 1 to 10 minutes. The reagent solution is supplemented with 0.5 to 50 µL aliquots, preferably 1 to 20 µL aliquots of test sample solutions. During incubation at a constant temperature, time-dependent changes in wavelength according to the color development of the chromogens are measured. A calibration curve prepared in advance can be used to determine the amount of the test substance in the specimen according to the principle of colorimetry.

Any of the enzymes (cholesterol esterase, cholesterol oxidase, and peroxidase) are used at a necessary amount ranging from preferably 0.2 to 20 U/mL, more preferably 1 to 10 U/mL.

When a measurement system is a solution, a surfactant used may be only the surfactant that preferentially dissolves high density lipoprotein (HDL). The surfactant is used at a concentration of preferably 0.01 to 5%, more preferably 0.1 to 1%.

Next, the constitution of a dry analytical element using a dry reagent as a measurement system will be described. The dry analytical element comprises at least one adhesive layer and one porous developing layer on a water-impermeable support.

The porous layer may be fibrous or non-fibrous. The porous layer functions as a developing layer for a liquid test sample and therefore, is preferably a layer having a liquid measurement effect. The liquid measurement effect is an effect by which the liquid test sample supplied by spotting onto the surface of the layer is spread in an almost constant amount per unit area in the direction of the surface of the layer without substantially unevenly distributing components contained in the test sample. The developing layer can comprise a hydrophilic polymer or surfactant as described in JP Patent Publication (Kokai) Nos. 60-222770A (1985), 63-219397A (1988), and 62-182652A (1987) in order to adjust a developing area, a developing rate, and so on.

Layers made of polyester fibers as typified by JP Patent Publication (Kokai) Nos. 55-164356A (1980), 57-66359A (1982), and 60-222769A (1985), etc. are preferable as the fibrous porous layer. Layers made of organic polymers such as polysulfonic acid are preferable as the non-fibrous porous layer.

The adhesive layer has a function of adhering to the water-impermeable support and the porous layer. Hydrophilic polymers such as gelatin and derivatives thereof (e.g., phthalated gelatin), cellulose derivatives (e.g., hydroxypropylcellulose), agarose, acrylamide polymers, methacrylamide polymers, and copolymers of acrylamide or methacrylamide and a variety of vinyl monomers can be utilized.

An aqueous solution containing the hydrophilic polymer is evenly applied to the support by a well known method. A method known in the art can be used as the application method. For example, dip coating, extrusion coating, doctor coating, hopper coating, curtain coating, or the like can be selected appropriately and used in the application.

The porous layer can be applied onto the adhesive layer. Preferably, a fabric provided in advance as knitting or porous film is laminated onto the adhesive layer. A laminating method is a method as described in JP Patent Publication (Kokai) No. 55-164356A (1980), in which the surface of the adhesive layer containing the hydrophilic polymer is made uniformly wet with water, and the fabric or porous film is laid on the surface and allowed to adhere thereto by slight and almost uniform pressure. The thickness of the adhesive layer is preferably 0.5 to 50 µm, more preferably 1 to 20 µm.

Preferable materials for the light-transmitting support are polyethylene terephthalate, polystyrene, and cellulose ethers such as cellulose triacetate. To allow a water absorption layer of the hydrophilic layer, a detection layer, a substantially non-porous reagent layer, and so on to firmly adhere to the support, the support is usually provided with an undercoat layer or subjected to a hydrophilizing treatment. The thickness of the support is not particularly limited and is preferably 10 to 1000 µm, more preferably 300 to 800 µm. When the support is light-transmitting, final detection may be performed on the support side or on the porous layer side. When the support is not light-transmitting, detection is performed from the porous layer side.

Next, a reagent composition for cholesterol measurement and a reagent composition that causes an optical change, which are used in the dry analytical element used in the measurement method of the present invention, will be described.

The reagent compositions may be contained in the first porous layer or may be contained both in the adhesive layer and in the porous layer. Alternatively, all or most of the reagent compositions may be contained in either of the layers or may be contained in layers other than the adhesive layer and the porous layer.

In the dry analytical element for HDL-C detection, any of the enzymes (cholesterol esterase derived from *Schizophyllum commune* or *Pseudomonas* sp. and cholesterol oxidase derived from *Pseudomonas* sp.) are used in an amount of preferably 0.1 to 20 kU per square meter, more preferably 0.5 to 10 kU per square meter.

Any of the two kinds of surfactants (i.e., the surfactant that preferentially dissolves HDL, and the surfactant that inhibits the lipoprotein other than HDL from dissolving) are supplied in an amount of preferably 0.2 to 20 g per square meter, more preferably 1 to 10 g per square meter. The amount ratio between the surfactant that preferentially dissolves HDL and the surfactant that inhibits the lipoprotein other than HDL from dissolving is preferably 9/1 to 5/5, more preferably 8/2 to 6/4.

Preferably, dextran sulfate (MW=5000000) combined with a magnesium ion is used as the aggregating agent that aggregates lipoprotein other than HDL, and is used in an amount of preferably 0.05 to 20 g per square meter in terms of dextran sulfate and 0.01 to 20 g per square meter in terms of magnesium chloride hexahydrate, more preferably 0.1 to 5 g/m$^2$ in terms of dextran sulfate and 0.5 to 10 g/m$^2$ in terms of magnesium chloride hexahydrate.

The peroxidase is not particularly limited by origin and, preferably, is derived from horseradish. The amount of the peroxidase used is preferably 1 to 100 kU/m$^2$, more preferably 10 to 50 kU/m$^2$.

A combination of 4-aminoantipyrine (4-AA) and the reagent that develops color through coupling therewith is preferable as the chromogens. Particularly preferably, DAOS is used. The amount of each of the chromogens (4-AA and hydrogen-donating coupling agent) used is preferably 0.1 to 10 g/m$^2$, more preferably 0.5 to 5 g/m$^2$.

Other reagent compositions for the dry analytical element for HDL-C detection can optionally contain a stabilizer, pH buffer, cross-linking agent (hardener or curing agent), surfactant, polymer and the like. These reagents can be contained in the adhesive layer or the porous layer of the dry analytical element of the present invention.

The pH of the buffer is determined depending on the optimum pH of the enzyme used and adjusted to preferably 5.0 to 8.0, more preferably 6.0 to 7.0.

For example, the dry analytical element of the present invention can be cut into small pieces such as a square of approximately 5 mm to approximately 30 mm on a side or a circle having almost the same size and used as a chemical analysis slide placed in a slide mount described in JP Patent Publication (Kokoku) No. 57-283331B (1982) (corresponding U.S. Pat. No. 4,169,751), JP Utility Model Publication (Kokai) No. 56-142454U (1981) (corresponding U.S. Pat. No. 4,387,990), JP Patent Publication (Kokai) No. 57-63452A (1982), JP Utility Model Publication (Kokai) No. 58-32350U (1983), JP Patent Publication (Kohyo) No. 58-501144A (1983) (corresponding International Publication No. WO083/00391), etc. This is preferable from the viewpoint of production, packaging, transport, storage, measurement procedures, and so on. Depending on the purpose of usage, the dry analytical element is placed in a long tape form in a cassette or magazine for use. Alternatively, the small piece thereof is placed in a container with an opening for use or attached to or placed in an aperture card for use. Alternatively, the small cut piece can also be used directly.

For example, an aqueous test sample solution is spotted in a range from approximately 2 μL to approximately 30 μL, preferably 4 μL to 15 μL, onto the porous developing layer for a liquid test sample in the dry analytical element of the present invention. The dry analytical element on which the test sample solution has been spotted is incubated at a constant temperature ranging from approximately 20° C. to approximately 45° C., preferably approximately 30° C. to approximately 40° C., for 1 to 10 minutes. Color development or discoloration within the dry analytical element is reflex-measured from the light-transmitting support side. A calibration curve prepared in advance can be used to determine the amount of the test substance in the specimen according to the principle of colorimetry.

The measurement procedures can be practiced according to exceedingly easy procedures using a chemical analyzer described in JP Patent Publication (Kokai) Nos. 60-125543A (1985), 60-220862A (1985), 61-294367A (1986), and 58-161867A (1983) (corresponding U.S. Pat. No. 4,424,191), etc. to achieve quantitative analysis with high precision. Depending on purposes and necessary precision, the degree of color development may be assessed by visual observation to perform semiquantitative measurement.

The dry analytical element of the present invention is stored in a dry state until analysis. Therefore, the reagents do not have to be prepared before use. Moreover, reagents in a dry state generally have high stability. Therefore, the method of the present invention is more convenient and rapid than a so-called solution method in which reagent solutions must be prepared before use. Moreover, the method of the present invention is also excellent as an examination method capable of rapid examination with high precision using a trace amount of liquid test samples.

The present invention will be described further specifically with reference to Examples below. However, the present invention is not intended to be limited to Examples.

EXAMPLES

Example 1

Measurement Example of Solution System Using Enzymes of the Present Invention

A reagent solution was prepared according to composition shown below.

| | |
|---|---|
| MES buffer (pH 7.0) | 700 mmlo/L |
| cholesterol esterase (derived from *Schizophyllum commune*) | 4.5 U/mL |
| cholesterol oxidase (derived from *Pseudomonas* sp.) | 2.8 U/mL |
| peroxidase | 4.8 U/mL |
| 4-aminoantipyrine (manufactured by Wako Pure Chemical Industries, Ltd.) | 4.0 mmol/L |
| DAOS (manufactured by DOJINDO Laboratories) | 4.0 mmol/L |
| EMULGEN B66 (manufactured by Kao Corp.) | 0.62 mg/mL |

Specimens used were test samples of purified HDL and LDL adjusted to a cholesterol concentration of 100 mg/dL, and 7% HAS aqueous solution. A 245 μL aliquot of the reagent solution was incubated in advance at 37° C. for 3 minutes and supplemented with 5 μL aliquots of the specimens, followed by measurement of color development states at 600 nm. As a result, the method caused HDL to completely develop color in approximately 5 minutes but caused no change in LDL, as shown in FIG. 1.

Comparative Example 1

Measurement Example of Solution System Using Cholesterol Esterase of an Alternative Origin A reagent solution was prepared according to the same formulation as in Example 1 except that only cholesterol esterase used was of the following origin:

| | |
|---|---|
| cholesterol esterase (derived from *Chromobacterium viscosum*) | 4.5 U/mL |

The same specimens as in Example 1 were used to perform measurement.

Figure 2:
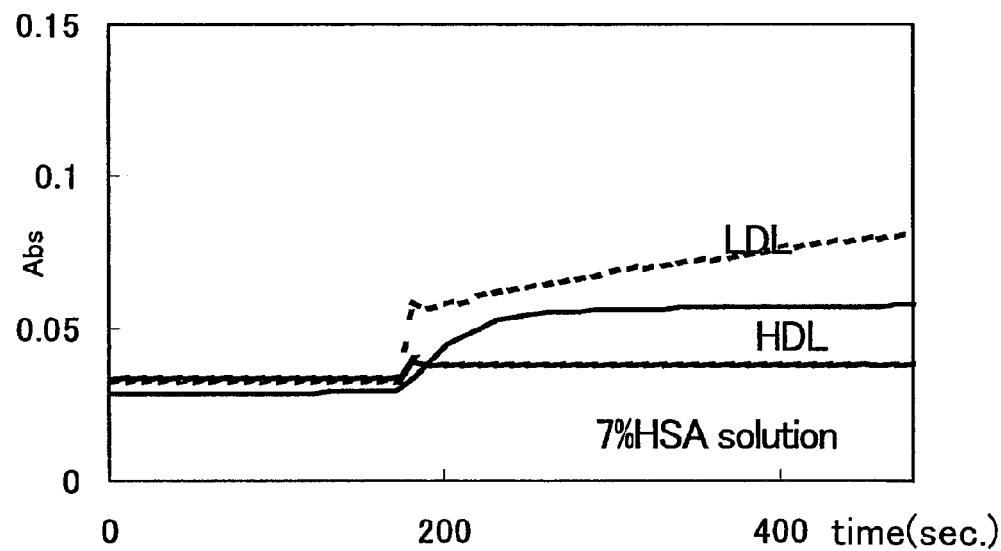
FIG. 2 shows a result of a measurement example (Comparative Example 1) of a solution system using cholesterol esterase of an alternative origin.

As a result, small sensitivity and low specificity were exhibited both to HDL and to LDL, as shown in FIG. 2.

Comparative Example 2

Measurement Example of Solution System Using Cholesterol Oxidase of an Alternative Origin A reagent solution was prepared according to the same formulation as in Example 1 except that only cholesterol oxidase used was of the following origin:

| | |
|---|---|
| cholesterol oxidase (derived from Microorganism) | 2.8 U/mL |

The same specimens as in Example 1 were used to perform measurement.

Figure 3:
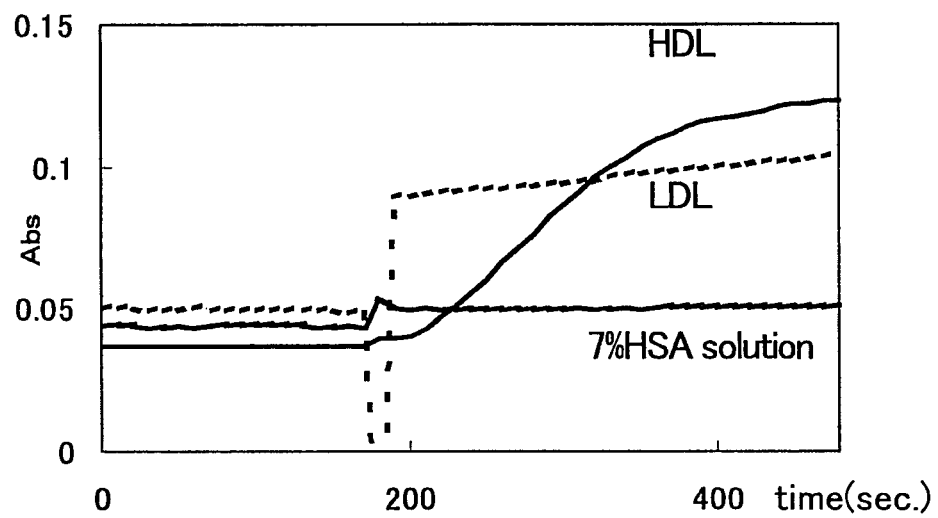
FIG. 3 shows a result of a measurement example (Comparative Example 2) of a solution system using cholesterol oxidase of an alternative origin.

As a result, small sensitivity and low specificity were exhibited both to HDL and to LDL, as shown in FIG. 3.

Comparative Example 3

Measurement Example of Solution System Using Cholesterol Esterase and Cholesterol Oxidase of Alternative Origins A reagent solution was prepared according to the same formulation as in Example 1 except that cholesterol esterase and cholesterol oxidase used were of the following origins:

| | |
|---|---|
| cholesterol esterase (derived from *Chromobacterium viscosum*) | 4.5 U/mL |
| cholesterol oxidase (derived from Microorganism) | 2.8 U/mL |

The same specimens as in Example 1 were used to perform measurement.

Figure 4:
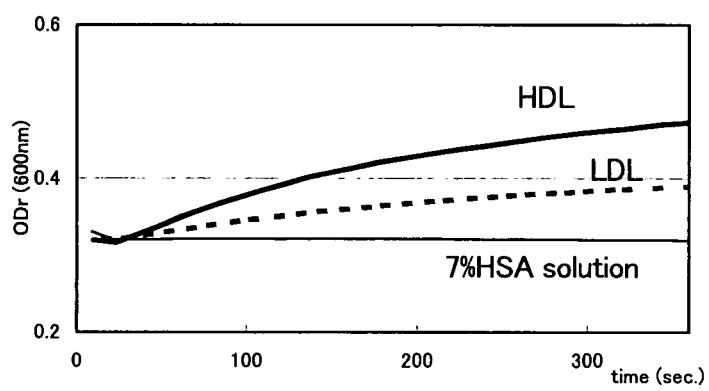
FIG. 4 shows a result of a measurement example (Comparative Example 3) of a solution system using cholesterol esterase and cholesterol oxidase of alternative origins.

As a result, small sensitivity and low specificity were exhibited both to HDL and to LDL, as shown in FIG. 4.

Example 2

Dry Analytical Element Using Enzymes of the Present Invention

A gelatin aqueous solution was applied at a thickness (after drying) of 14 μm to a 180-μm colorless and transparent flat film of polyethylene terephthalate which was undercoated with gelatin, followed by drying. Water was supplied at a supply rate of approximately 30 g/m² to all over the surface of the film to make the surface wet. Then, a 36-gauge tricot knitting fabric made of polyester spun yarn corresponding to 50 deniers was slightly pressed and stacked thereon, followed by drying. Next, an aqueous solution with a composition shown below was applied onto the fabric, followed by drying.

| | |
|---|---|
| MES buffer (pH 6.6) | 18 g/m² |
| cholesterol esterase (derived from *Schizophyllum commune*) | 1.9 kU/m² |
| cholesterol oxidase (derived from *Pseudomonas* sp.) | 1.2 kU/m² |
| peroxidase | 31 kU/m² |
| 4-aminoantipyrine (manufactured by Wako Pure Chemical Industries, Ltd.) | 0.4 g/m² |
| DAOS (manufactured by DOJINDO Laboratories) | 0.4 g/m² |
| Emulgen B66 (manufactured by Kao Corp.) | 2.0 g/m² |
| Pluronic F-88 (manufactured by ADEKA Corp.) | 1.3 g/m² |
| dextran sulfate (5000,000) (manufactured by Wako Pure Chemical Industries, Ltd.) | 0.7 g/m² |
| magnesium chloride hexahydrate(manufactured by Wako Pure Chemical Industries, Ltd.) | 4.6 g/m² |

Figure 5:
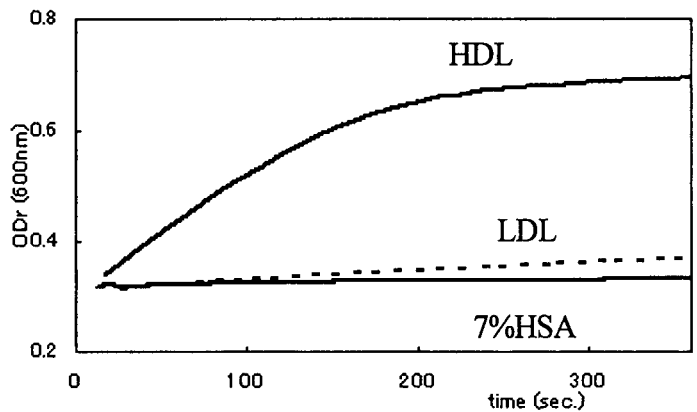
FIG. 5 shows a result of a measurement example (Example 2) with a dry analytical element using the enzymes of the present invention.

Specimens used were test samples of purified HDL and LDL adjusted to a cholesterol concentration of 100 mg/dL, and 7% HSA aqueous solution. To the dry analytical element, 10 μL aliquots of the specimens were spotted and then incubated at 37° C. for 6 minutes. In this procedure, color development states at 600 nm were measured. As a result, the method caused HDL to completely develop color in approximately 5 minutes but caused no change in the OD of LDL, as shown in FIG. 5.

Figure 6:
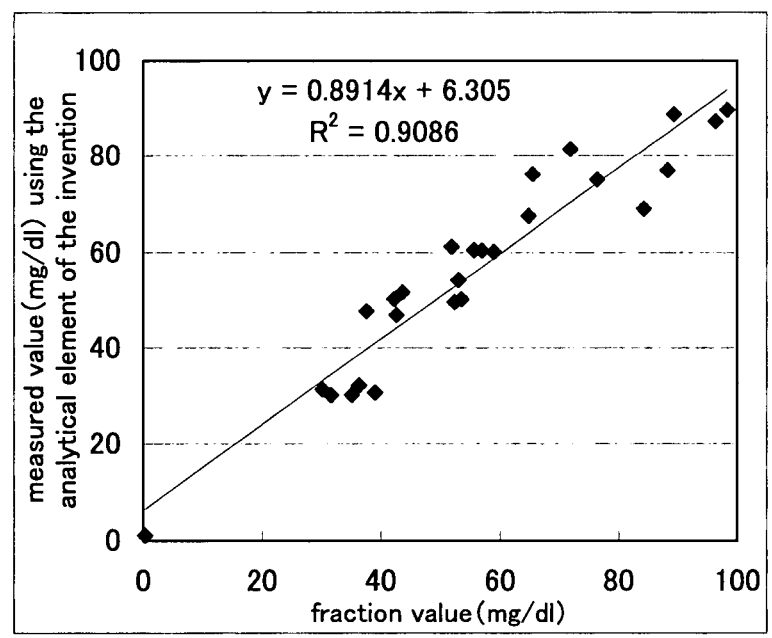
FIG. 6 shows a result of examination of the multiple sample correlation between the method of the present invention and the separation method with phosphotungstic acid.

Twenty-five healthy individuals were examined for the multiple sample correlation between the method of the present invention and the separation method with phosphotungstic acid. As a result, the method of the present invention could obtain favorable correlation when compared with the reference method, as shown in FIG. 6.

Comparative Example 4

A dry analytical element was produced in the same way as in Example 2 except that cholesterol esterase and cholesterol oxidase used were of the following origins:

| | |
|---|---|
| cholesterol esterase (derived from *Chromobacterium viscosum*) | 1.9 U/m² |
| cholesterol oxidase (derived from Microorganism) | 1.2 U/m² |

The same specimens as in Example 2 were used and measured in the same way as in Example 2.

Figure 7:
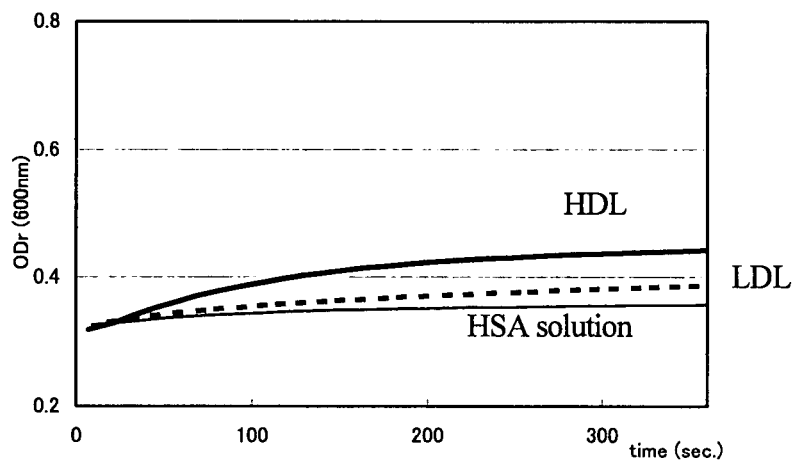
FIG. 7 shows a result of a measurement example (Comparative Example 4) with a dry analytical element using cholesterol esterase and cholesterol oxidase of alternative origins.
Figure 8:
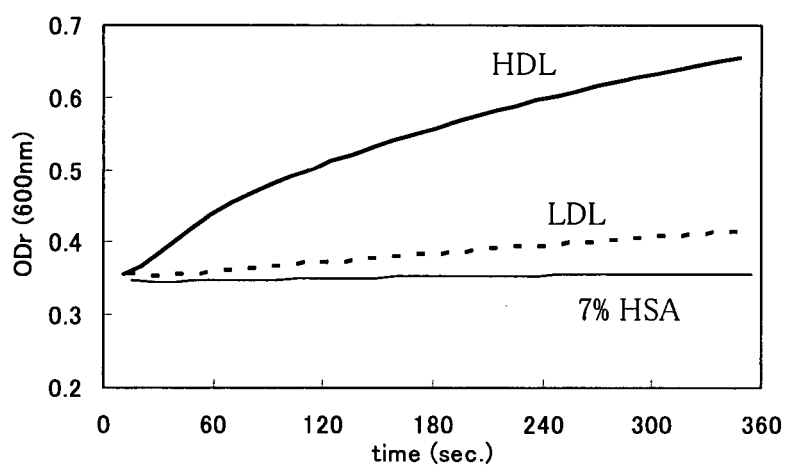
FIG. 8 shows a result of a measurement example (Example 3, Pegnol 005) with a dry analytical element using the enzymes of the present invention.
Figure 9:
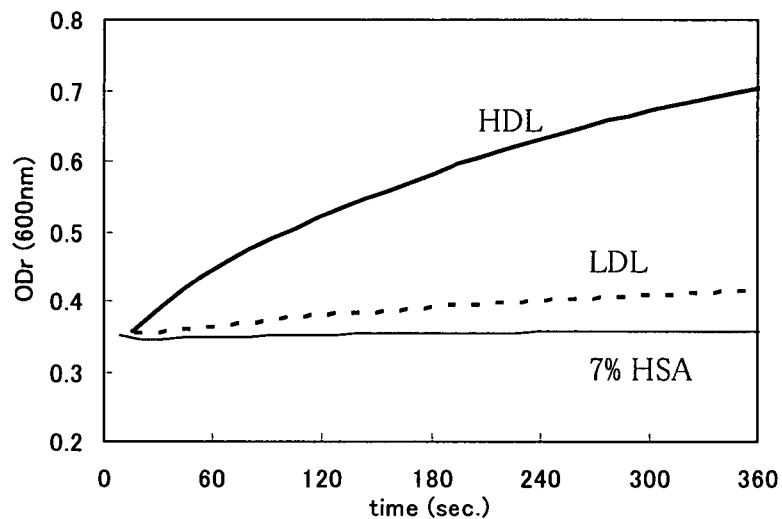
FIG. 9 shows a result of a measurement example (Example 3, PIONIND-6512) with a dry analytical element using the enzymes of the present invention.
Figure 10:
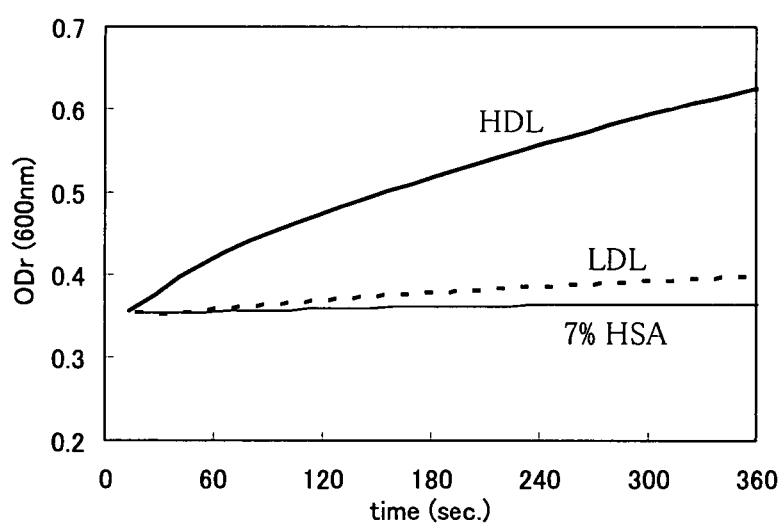
FIG. 10 shows a result of a measurement example (Example 3, Emulgen A90) with a dry analytical element using the enzymes of the present invention.
Figure 11:
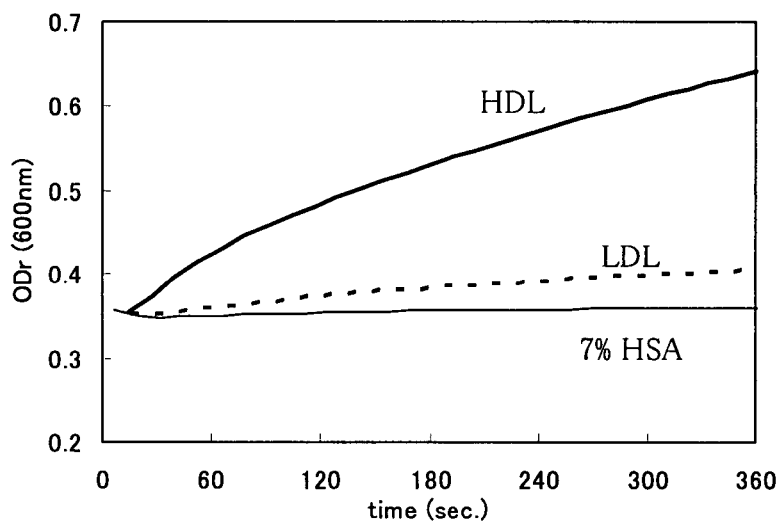
FIG. 11 shows a result of a measurement example (Example 3, Noigen EA-157) with a dry analytical element using the enzymes of the present invention.
Figure 12:
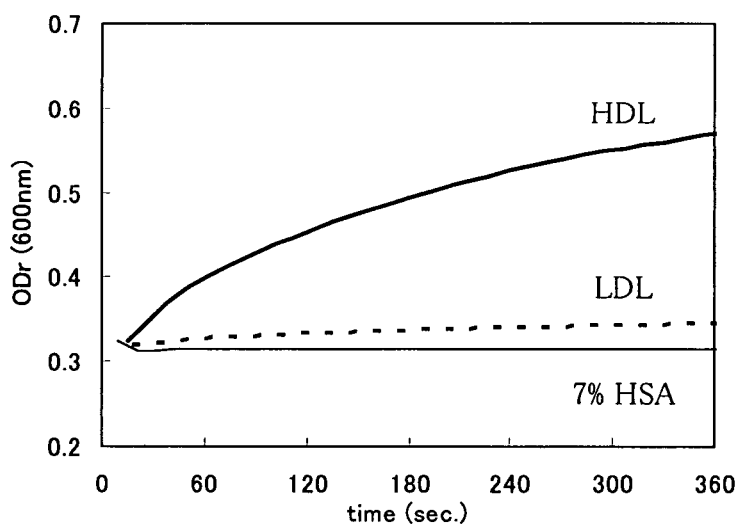
FIG. 12 shows a result of a measurement example (Example 3, Sorpol T20) with a dry analytical element using the enzymes of the present invention.

As a result, the analytical element thus produced exhibited low reactivity both to HDL and to LDL and no specificity to HDL, as shown in FIG. 7.

Example 3

Dry Analytical Element (2) Using Enzymes of the Present Invention

Dry analytical elements were produced in the same way as in Example 2 except that Emulgen B66 in Example 2 was replaced with Pegnol 005 (manufactured by TOHO Chemical Industry Co., Ltd), PIONIN D-6512 (manufactured by Takemoto Oil & Fat Co., Ltd), Emulgen A90 (manufactured by Kao Corp.), Noigen EA-157 (manufactured by Dai-ich Kogyo Seiyaku Co., Ltd), and Sorpol T20 (manufactured by TOHO Chemical Industry Co., Ltd), respectively.

Specimens used were test samples of purified HDL and LDL adjusted to a cholesterol concentration of 100 mg/dL, and 7% HSA aqueous solution. To the dry analytical element, 10 μL aliquots of the specimens were spotted and then incubated at 37° C. for 6 minutes. In this procedure, color development states at 600 nm were measured. As a result, the method caused HDL to completely develop color in approximately 5 minutes but caused no change in the OD of LDL, as shown in FIGS. 8 to 12.

EFFECT OF THE INVENTION

The method for measuring HDL-C of the present invention allowed for the convenient, rapid, and selective measurement of HDL-C in a specimen.

The invention claimed is:

1. A dry analytical element for high density lipoprotein cholesterol (HDL-C) detection which consists of a water-impermeable support, an adhesive layer which is composed of gelatin, and a porous developing layer which is composed of polyester or polysulfone, wherein the porous developing layer comprises cholesterol esterase derived from *Schizophyllum commune*, cholesterol oxidase derived from *Pseudomonas* sp., a surfactant that preferentially dissolves high density lipoprotein (HDL), peroxidase and chromogens,
wherein the surfactant that preferentially dissolves HDL is polyoxyethylene alkylene phenyl ether or polyoxyethylene alkylene tribenzyl phenyl ether, and wherein the chromogens are 4-aminoantipyrine or a derivative thereof and a Trinder reagent that couples with the 4-aminoantipyrine or the derivative thereof.

2. The dry analytical element according to claim 1, wherein the polyoxyethylene alkylene phenyl ether is polyoxyethylene styryl phenyl ether, and the polyoxyethylene alkylene tribenzyl phenyl ether is polyoxyethylene tribenzyl phenyl ether.

3. The dry analytical element according to claim 2, wherein the polyoxyethylene styryl phenyl ether is polyoxyethylene mono-, di-, or tri-styryl phenyl ether.

4. The dry analytical element according to claim 1, wherein a surfactant that inhibits a lipoprotein other than HDL from dissolving and/or an aggregating agent that aggregates lipoprotein other than HDL are contained in at least one layer on the water-impermeable support.

5. The dry analytical element according to claim 4, wherein the surfactant that inhibits the lipoprotein other than HDL from dissolving is polyoxyethylene alkyl ether sulfate, alkylbenzene sulfonate, or a polyoxyethylene-polyoxypropylene condensate.

6. The dry analytical element according to claim 4, wherein the aggregating agent that aggregates lipoprotein other than HDL is phosphotungstic acid or a salt thereof combined with a divalent metal ion, dextran sulfate combined with a divalent metal ion, heparin combined with a divalent metal ion, or polyoxyethylene.

7. A method for measuring high density lipoprotein cholesterol (HDL-C) in a body fluid test sample, which comprises:

spotting the body fluid test sample onto the dry analytical element according to claim 1, and measuring color development state.

* * * * *